US00PP36606P2

(12) United States Plant Patent
Bakhuijzen et al.

(10) Patent No.: US PP36,606 P2
(45) Date of Patent: Apr. 15, 2025

(54) ***CORTADERIA* PLANT NAMED 'Day10'**

(50) Latin Name: *Cortaderia selloana*
Varietal Denomination: Day10

(71) Applicants: David Bakhuijzen, Boskoop (NL); Marcel de Pater, Boskoop (NL)

(72) Inventors: David Bakhuijzen, Boskoop (NL); Marcel de Pater, Boskoop (NL)

(73) Assignee: V.O.F. DAYLIGHT BOOMKWEKERIJ, Boskoop (NL)

( * ) Notice: Subject to any disclaimer, the term of this patent is extended or adjusted under 35 U.S.C. 154(b) by 0 days.

(21) Appl. No.: 18/913,302

(22) Filed: Oct. 11, 2024

(51) Int. Cl.
*A01H 5/02* (2018.01)
*A01H 6/00* (2018.01)

(52) U.S. Cl.
USPC ..... Plt./384
CPC ..... *A01H 6/00* (2018.05)

(58) Field of Classification Search
USPC ..... Plt./384
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Cortaderia* plant named 'Day10' that is characterized by its strong and sturdy plant habit, its conspicuously dense and compact plant shape, and its floriferous flowering habit with beige-white inflorescences.

3 Drawing Sheets

Botanical classification: *Cortaderia selloana.*
Cultivar designation: 'Day10'.

BACKGROUND OF THE INVENTION

The present invention relates to a new and distinct cultivar of *Cortaderia selloana* and will be referred to hereafter by its cultivar name, 'Day10'. 'Day10' represents a new perennial ornamental grass grown for landscape use.

'Day10' was discovered by the Inventors as a naturally occurring branch mutation of *Cortaderia selloana* 'Pumila' (not patented) that was growing in a production field in Boskoop, The Netherlands in July of 2020.

Asexual propagation of the new cultivar was first accomplished by division by one of the Inventors in July of 2020 in Boskoop, The Netherlands. Asexual propagation by division has determined that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'Day10' as a unique cultivar of *Cortaderia.*

1. 'Day10' exhibits a strong and sturdy plant habit.
2. 'Day10' exhibits a conspicuously dense and compact plant shape.
3. 'Day10' exhibits a floriferous flowering habit with beige-white inflorescences.

The parent plant of 'Day10' differs from 'Day10' in having a taller plant height (twice the size), less inflorescences, and flowering that is not consistent. 'Day10' can be most closely compared to the *Cortaderia* cultivars 'Junior' (not patented), 'Vercor3' (not patented), and 'Day 20'. 'Junior' is similar to 'Day10' in foliage and flower color. 'Junior' differs from 'Day10' in having a taller plant height, larger inflorescences, and flower scapes that lack anthocyanin coloration. 'Vercor3' differs from 'Day10' in having a taller plant height, a less dense (more open) and less compact plant habit, less inflorescences, and flowering that is not consistent. 'Day 20' is similar to 'Day10' in having a dense and compact plant shape and a floriferous plant habit. 'Day 20' differs from 'Day10' in having variegated foliage and creamy white inflorescences.

BRIEF DESCRIPTION OF THE DRAWINGS

The accompanying color photographs illustrate the overall appearance and distinct characteristics of the new *Cortaderia*. The photographs were taken of a plant 1-years-in-age as grown outdoors in a 21-cm container in Boskoop, The Netherlands.

The photograph in FIG. 1. provides a side view of a plant of 'Day10' in bloom.

Figure 1:
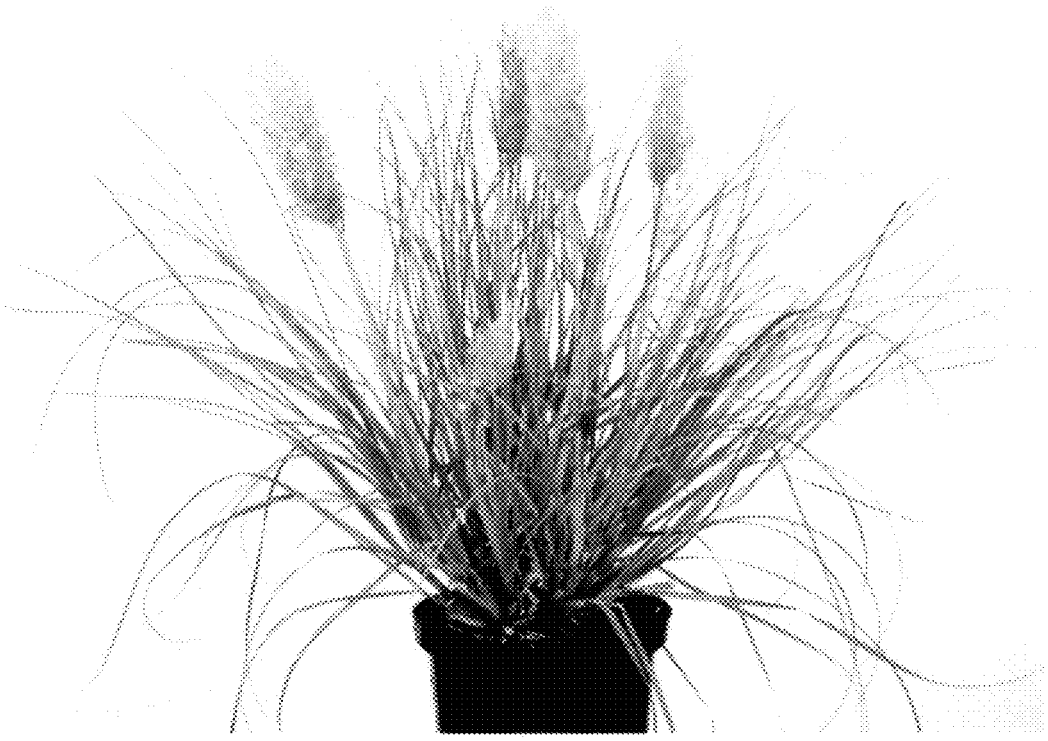
Figure 2:
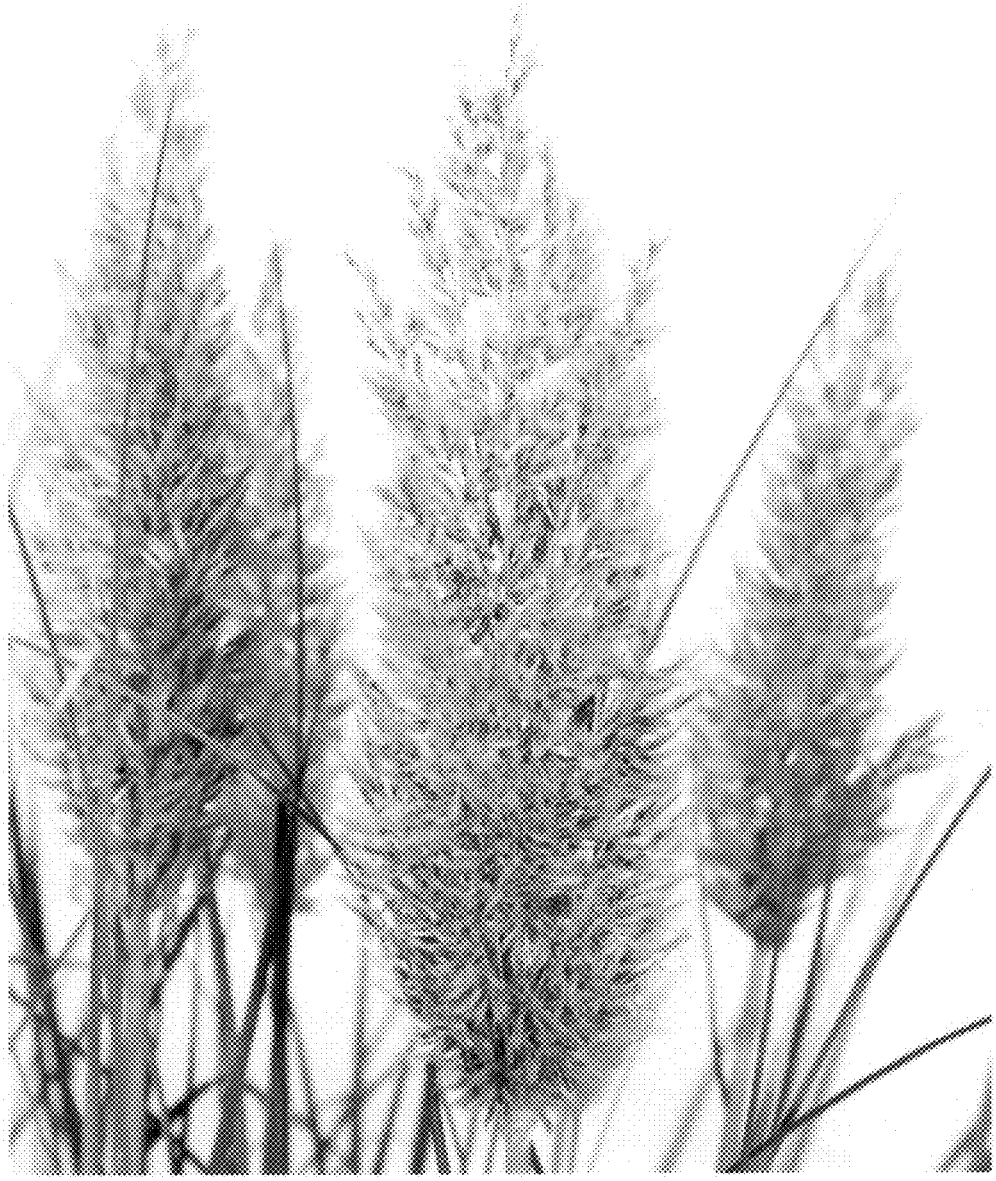

The photograph in FIG. 2. provides a close-up view of the inflorescences of 'Day10'.

Figure 3:
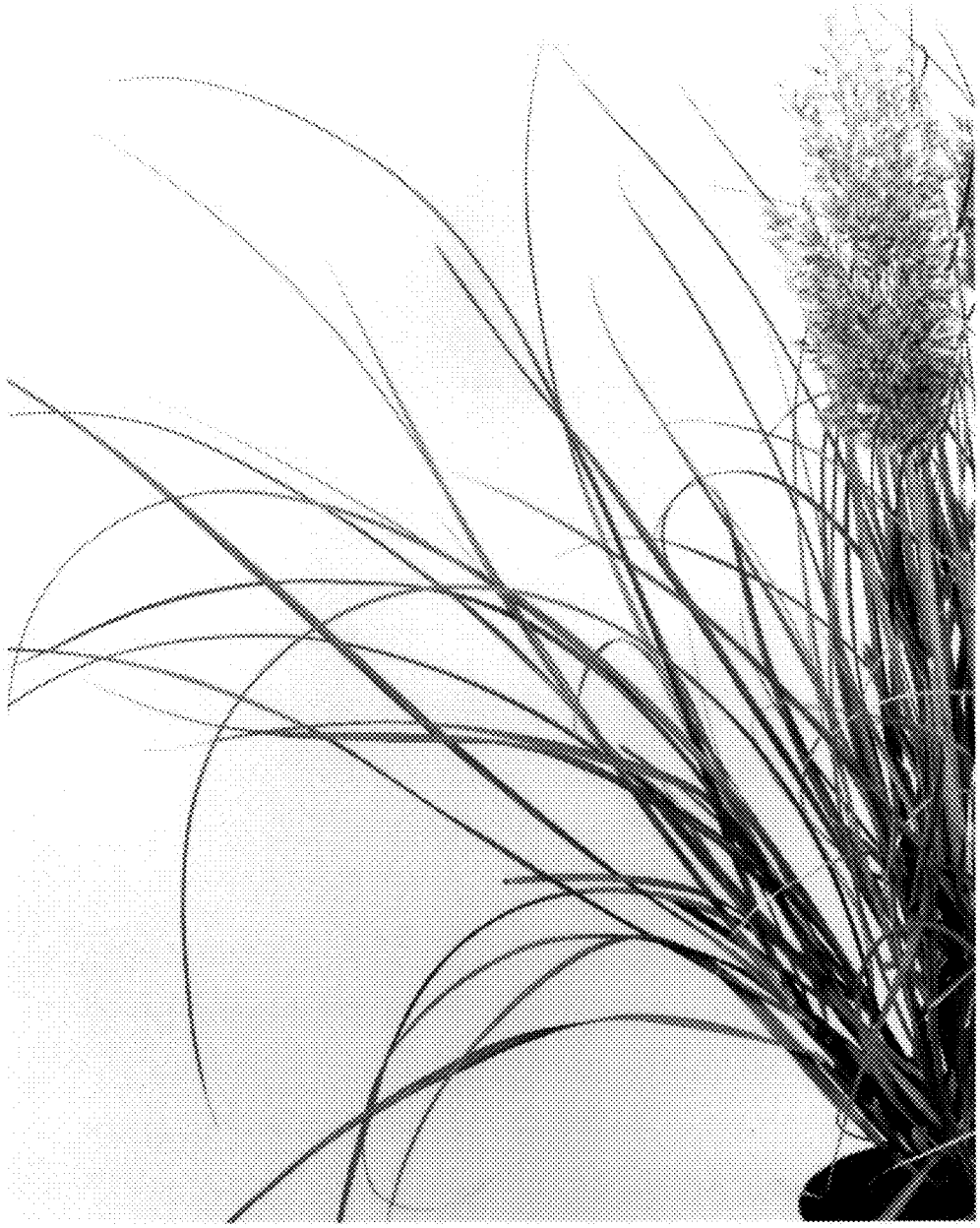

The photograph in FIG. 3. provides a close-up view of the foliage of 'Day10'.

The colors in the photographs are as close as possible with the photographic and printing technology utilized and the color values cited in the Detailed Botanical Description accurately describe the colors of the new *Cortaderia.*

DETAILED BOTANICAL DESCRIPTION

The following is a detailed description of 1-year-old plants of the new cultivar as grown outdoors in a 21-cm circular container in Boskoop, The Netherlands. The phenotype of the new cultivar may vary with variations in environmental, climatic, and cultural conditions, as it has not been tested under all possible environmental conditions. The color determination is in accordance with The 2019 Colour Chart of The Royal Horticultural Society, London, England, except where general color terms of ordinary dictionary significance are used.

General description:

*Blooming period.*—8 weeks; late summer into fall in The Netherlands.

*Plant type.*—Herbaceous, ornamental perennial grass.

*Plant habit.*—Clump-forming, dense, compact, upright with cascading foliage.

*Height and spread.*—Average of 59 cm in height from the soil level to the top of the foliar plane, average of 56 cm in height from the soil level to the top of the floral plane, 1.9 m in diameter as grown in a container and 1 m in height and spread as grown in the landscape.

*Cold hardiness.*—At least in U.S.D.A. Zone 7.

*Diseases and pests.*—No susceptibility or resistance to diseases or pests has been observed.

*Root description.*—Thin, fleshy, no stolons or rhizomes present.

*Root development.*—Average of 8 weeks to produce a young rooted plant in spring from a division.

*Propagation.*—Division.

*Growth rate.*—Moderate to highly vigorous.

Branch description (basal shoots):

*Branching.*—Average of 43 basal shoots.

*Branch size.*—8.7 cm in length (consisting of sheaths; measured from base of shoot to base of uppermost leaf blade), 4.5 cm in diameter.

*Branch shape.*—Rounded.

*Branch surface.*—Slightly glossy

*Branch strength.*—Very strong.

*Branch color.*—Young; 145A, mature; 176B, internodes; N144.

*Branch aspect.*—Average angle: 35° (varying between 0° (=vertical) and 70°).

*Internode length.*—3 mm.

Foliage description:

*Leaf shape.*—Linear.

*Leaf division.*—Simple.

*Leaf base.*—Sheathing; 8.7 cm in length, 4.5 mm in width, color; 176B.

*Leaf apex.*—Narrow and long acuminate.

*Leaf aspect.*—Moderately carinate.

*Leaf venation.*—Parallel, upper surface 138B, lower surface 144B.

*Leaf margins.*—Entire, but very sharp when rubbed downwards; due to very small and very sharp teeth.

*Leaf size.*—46.8 cm in length, 6 mm in width.

*Leaf (blade and sheath) surface.*—Both surfaces non-rugose, matte, glabrous and smooth, ligules hairy, average length of hairs is 1 mm, NN155B in color.

*Leaf arrangement.*—Alternate.

*Leaf color.*—Young upper surface; a blend of N144D and 145A, young lower surface; 144B, mature upper surface N138B, mature lower surface; a blend of 137A and NN137B.

Flower description:

*General description.*—Compact, panicle.

*Lastingness of inflorescence.*—Average of 1 month for spikelets to drop, persistent.

*Fragrance.*—None.

*Panicle size.*—Average of 18.3 cm in length and 6.9 cm in diameter.

*Flower number.*—An average of 2,500 flowers per inflorescence, 17,500 flowers per plant.

*Flower buds.*—An average of 2 mm in length, enclosed by 1 palea, 1 awn and many lemma, average length 9 mm, 1 mm in diameter, linear in shape, smooth and glabrous surface, matte, color; 145C with glume and lemma a color between 156D and 157D.

*Peduncle.*—44 cm in length, 3.5 mm in diameter, very strong, held in an angle of 10° to soil level, surface smooth, matte, glabrous, and N144A in color.

*Pedicels.*—1.5 mm in length, 0.5 mm in diameter, moderately strong, held in an angle of 10° to soil level, surface smooth, matte, glabrous, and 148D in color.

*Spikelet description (flowers).*—Spikelet consisting of a single palea; shaped linear, 3 mm in length, 1 mm in width, top narrow acute, base cuneate, margins entire, both surfaces N144A in color, single awn elongated to an average of 9 mm in length, glabrous, slightly glossy, 156C in color, many lemma placed at the base of each palea; hair-like, average of 6 mm in length, 156D in color.

Reproductive organs:

*Androecium.*—Stamens; average of 2, anthers; basifixed and feather-like in shape, 1.5 mm in length, 0.4 mm in width, N199B in color, filament; 1 mm in length, 199A in color, pollen; none observed.

*Gynoecium.*—Pistil; none observed.

*Seed.*—None observed.

It is claimed:

1. A new and distinct cultivar of *Cortaderia* plant named 'Day10' as herein illustrated and described.

* * * * *